United States Patent [19]

Mackay et al.

[11] Patent Number: 5,170,367
[45] Date of Patent: Dec. 8, 1992

[54] NONDESTRUCTIVE DETERMINATION OF PHASE FRACTIONS OF COMPOSITE MATERIALS

[75] Inventors: Kirk R. Mackay, San Diego, Calif.; Lawrence R. Norpoth, Greer, S.C.

[73] Assignee: The Expert System Technologies, Inc., San Diego, Calif.

[21] Appl. No.: 514,088

[22] Filed: Apr. 25, 1990

[51] Int. Cl.$^5$ .............................................. G06F 15/20
[52] U.S. Cl. ................................ 364/571.01; 73/597; 364/571.02
[58] Field of Search ............. 73/597; 364/554, 571.01, 364/571.02

[56] References Cited

U.S. PATENT DOCUMENTS

| | | | |
|---|---|---|---|
| 4,794,545 | 12/1988 | Salvado | 364/497 |
| 4,856,335 | 8/1989 | Tornberg | 73/597 |
| 4,961,346 | 10/1990 | Salvado et al. | 73/644 |

OTHER PUBLICATIONS

N. R. Draper et al., "Applied Regression Analysis", 1966, John Wiley & Son, pp. 313-325.
Arthur E. Hoerl et al., "Ridge Regression: Biased Estimation for Nonorthogonal Problems," Technometrics, vol. 12, pp. 55-67 (1970).
Arthur E. Hoerl et al., "Ridge Regression: Applications to Nonorthogonal Problems", Technometrics, vol. 12, pp. 69-82 (1970).

*Primary Examiner*—Parshotam S. Lall
*Assistant Examiner*—Edward R. Cosimano
*Attorney, Agent, or Firm*—Gregory Garmong

[57] ABSTRACT

The fractions of the phases of a composite material are determined utilizing a calibration relationship between at least one nondestructively measured quantity and a destructively measured phase fraction. The proper calibration relationship is selected from a multiple-variable regression relation, a single-variable regression of a product of two measured quantities, one of two single-variable regressions, or a weighted average of the results of two single-variable regressions, all four approaches utilizing nondestructive measurements of specimen consolidated height and specimen consolidated ultrasonic transit time. When prepreg material having uniaxial fibers is analyzed, multiple-layer specimens are formed by stacking the individual plies so that the fiber directions in adjacent layers are not parallel.

19 Claims, 9 Drawing Sheets

NONDESTRUCTIVE DETERMINATION OF PHASE FRACTIONS OF COMPOSITE MATERIALS

BACKGROUND OF THE INVENTION

This invention relates to the nondestructive measurement of the fractions of phases present in composite materials, and, more particularly, to calibration relationships and specimen preparation techniques useful in such measurement.

Composite materials are mixtures of two or more phases in which the components retain their inherent character within the mixture. Such materials can, when properly engineered, provide properties that are superior to those that could be obtained from the individual phases acting alone. In just twenty years, advanced composite materials of high performance fibers within a nonmetallic matrix have become standard materials of construction for aerospace and other applications, because of their superior strength-to-weight and modulus-to-weight properties.

Composite materials have the additional desirable feature of permitting the material of construction of a structure to be tailored precisely to the requirements of the structure, and even to the requirements of different parts of the structure. For example, different regions of a composite aircraft wing can be made from different materials to meet modulus or strength limitations, as needed. The fractions of the phases in the different regions can also be varied as needed, as can the arrangement of the fibers. The designer of a composite structure has more degrees of freedom in specifying the exact nature of the material of construction than possible with non-composite materials, and can therefore more precisely meet the needs of the design.

When composite materials are fabricated or used, there is generally no question as to the nature of the constituents. There can be, however, some doubt as to the fractions of the phases present. The machines that manufacture the nonmetallic composite materials in a form known as a "prepreg" usually supply a known amount of fiber material per unit time in a continuous manner, and the nonmetallic matrix material is infused around the fibers. One objective of the manufacturing process is to supply an exactly controlled amount of fiber material and matrix material, thereby exactly determining the relative fractions of the phases. However, with present manufacturing technology, there is inevitably some variation in the amounts added, leading to variations in the fractions of the phases present.

Aerospace designers have developed acceptance standards requiring that the fractions of the phases be supplied to within specific tolerances, currently +/−2 to 3 percentage points. For example, the designer may specify that a composite material include precisely 36.4 +/−2.0 percent by weight of resin matrix phase. If the manufacturer supplies a composite material having less than 34.4 or more than 38.4 percent by weight of matrix phase, the material is rejected. For some applications, even these tolerances are too large, and in those cases the designers would prefer tolerances of as small as +/−0.5 percentage points.

Because of the need to known the amount of phases present to be certain that they are within the specified standards, it is critically important to the manufacturers of composite materials that they be able to measure the fraction of the phases present in the prepreg composite material during manufacture to ensure that unacceptable material is not shipped to customers. It is equally important to the users of the prepreg composite material to be able to independently check the fraction of the phases present in the material received, to be certain that the acceptance criteria are met.

For years, the standard approach to determine the fractions of the phases was to excise a piece of the composite material, weigh the piece, dissolve or burn away the matrix, and weigh the residue that was assumed to be the fiber material. This approach suffers from several drawbacks, including its destructive character, lack of reproducibility, and use of noxious chemicals or production of noxious gases during removal of the matrix. This technique is also quite slow and expensive, and is not adapted to feedback control of the manufacturing operation.

To avoid these disadvantages, a nondestructive rationing approach was developed. The thickness of a working specimen is measured, and the fraction of the phases determined as the ratio of the thickness of the working specimen to a previously measured baseline specimen, times the destructively measured phase fraction of the baseline specimen. However, thickness of a piece is not a material property. The results obtained with this technique are therefore not meaningful, unless it is assumed that the areal weight of fiber in the baseline specimen is the same as in the working specimen, an assumption that can sometimes be valid in specimens taken from a manufacturing machine whose operating parameters are not varied in the slightest, and therefor the fiber content is precisely the same for the specimens. The assumption is often not valid in manufacturing operations, and is valid only fortuitously for composite materials from different lots and/or different manufacturers. The operability of this technique is thus dependent upon assumptions about the results, an undesirable situation.

More recently, a nondestructive technique preferably using ultrasonic measurements and a calibration relationship was introduced, see U.S. Pat. No. 4,794,545 and allowed Application Ser. No. 07/290,810, now U.S. Pat. No. 4,961,346, whose disclosures are incorporated by reference. A refinement to the technique improved its accuracy, see U.S. Pat. No. 4,856,335, whose disclosure is incorporated by reference.

In the preferred approach according to these patents, an ultrasonic wave is passed through a calibration specimen and some property such as ultrasonic slowness determined. The fraction of the phases is measured by the destructive measurement approach, and the ultrasonic measurement correlated with the destructively measured phase fraction. At least two, and preferably a large number, of the calibration specimens are measured, and the results combined as a calibration relationship. Then the same ultrasonic property is measured on a working specimen, and the phase fraction determined from the calibration relationship. This technique has been verified on a large number of composite material systems, and provides measurements of phase fractions accurate to within +/−0.5 percentage points, or even better, for many composite materials systems.

However, some composite materials systems have been identified wherein the measurements are not consistently accurate to within the required limits. Moreover, in those systems wherein the required accuracies can be achieved, it would be desirable to achieve even better accuracies. Thus, there is a continuing need for a further improved methodology for analyzing the fractions of the phases of composite materials by nondestructive procedures. The present invention fulfills this need, and further provides related advantages.

SUMMARY OF THE INVENTION

For a wide variety of composite materials systems, the present invention provides methods for determining the fractions of the phases to accuracies consistently better than previously obtained. Existing measurement devices are used, and the improvements flow from the manner in which these technologies are applied. The approaches also permit detection of apparatus errors such as component failure that cause errors in the results.

The present invention provides an improved analytical scheme for developing and applying the calibration relationships used in the approach described in the '545 patent, which may also be used independently of the '545 patent. Additionally, for the commercially significant case of unidirectional prepreg material, the invention provides a new technique for specimen preparation of the calibration specimens that has been found to give superior results to alternative approaches.

In accordance with the invention, a method for establishing a primary calibration relationship useful in finding the fraction of phases present in a composite material comprises the steps of establishing a first calibration relation between a consolidated height of a specimen of a composite material and the fraction of phases in the specimen by the substeps of pressing the specimen between two probes with a pressure sufficient to remove voids that may be present in the composite material prior to the application of the pressure and measuring the height of the specimen between the probes, destroying the specimen and measuring the fraction of phases present in the specimen, repeating the steps of pressing and measuring the height, and destroying for at least two specimens, to form a first regression data set, performing a single variable regression between the measured height of the specimen and the measured fraction of phases present in the specimen for the first regression data set, to form a first calibration relation; establishing a second calibration relation between a consolidated ultrasonic transit time of a specimen of a composite material and the fraction of phases in the specimen by the substeps of pressing the specimen between two probes with a pressure sufficient to remove voids that may be present in the composite material prior to the application of the pressure and measuring the ultrasonic transit time through the thickness of the specimen between the probes, destroying the specimen and measuring the fraction of phases present in the specimen, repeating the steps of pressing and measuring the ultrasonic transit time, and destroying for at least two specimens, to form a second regression data set, performing a single variable regression between the measured ultrasonic transit time of the specimen and the measured fraction of phases present in the specimen for the second regression data set, to form a second calibration relation; and selecting as the primary calibration relation either the first or the second calibration relation, the selection being based upon the absence of multiple roots of the calibration relation, a positive slope to the calibration relation over a range of fractions of phases of interest, and the correlation coefficient of the calibration relation.

The approach requires that two different calibration relations be formed and evaluated, and the better selected as the primary calibration relationship. One of the calibration relations is between specimen height and phase fraction, and the other is between ultrasonic transit time and phase fraction, both relations determined while the specimen is compressed sufficiently to remove voids present in the composite material. For a prepreg material, the specimens will normally be compressed at least about 5-10 percent, while for a cured composite material very little if any compressive deformation is typically required.

It has been found that in some cases the specimen height calibration is more suitable than the ultrasonic transit time calibration, and in other cases the reverse is true. At this time, the identity of the more suitable calibration technique cannot be predicted from first principles, and it is therefore necessary to form and evaluate both relationships before selecting one. All of the measured data is therefore used in the analysis of working specimens, some directly and some only to the extent of ruling out one of the calibration relations.

In yet other cases, both the specimen thickness calibration and the ultrasonic transit time calibration yield good correlations and are suitable. In those instances, both calibrations can be used in the primary calibration, with a weighted average result of the two approaches used as the phase fraction. In accordance with this aspect of the invention, a method for establishing a primary calibration relationship useful in finding the fraction of phases present in a composite material comprises the steps of establishing a first calibration relation between a consolidated height of a specimen of a composite material and the fraction of phases in the speciment by the substeps of pressing the specimen between two probes with a pressure sufficient to remove voids that may be present in the composite material prior to the application of the pressure and measuring the height of the specimen between the probes, destroying the specimen and measuring the fraction of phases present in the specimen, repeating the steps of pressing and measuring the height, and destroying for at least two specimens, to form a first regression data set, performing a single variable regression between the measured height of the specimen and the measured fraction of phases present in the specimen for the first regression data set, to form a first calibration relation; establishing a second calibration relation between a consolidated ultrasonic transit time of a specimen of a composite material and the fraction of phases in the specimen by the substeps of pressing the specimen between two probes with a pressure sufficient to remove voids that may be present in the composite material prior to the application of the pressure and measuring the ultrasonic transit time through the thickness of the specimen between the probes, destroying the specimen and measuring the fraction of phases present in the specimen, repeating the steps of pressing and measuring the ultrasonic transit time, and destroying for at least two specimens, to form a second regression data set, performing a single variable regression between the measured ultrasonic transit time of the speciemen and the measured fraction of phases present in the specimen for the second regression data set, to form a second calibration relation; and selecting as the primary calibration relation the combination of the first and the second calibration relations, the phase fraction for a working specimen being a weighted average of the phase fractions independently determined from the first and the second calibration relations.

Another technique to utilize all of the information is to multiply the two measured values of specimen height and ultrasonic transit time together, and then perform a single variable regression of the product. In accordance with this aspect of the invention, a method for establishing a primary calibration relationship useful in finding the fraction of phases present in a composite material comprises the steps of pressing the specimen between two probes with a pressure sufficient to remove voids that may be present in the composite material prior to the application of the pressure, and, while so pressing, measuring the height of the specimen between the probes, and measuring the ultrasonic transit time through the thickness of the specimen in the region between the probes; multiplying the measured height of the specimen times the measured ultrasonic transit time to form a carrier variable; destroying the specimen and measuring the fraction of phases present in the specimen; repeating the steps of pressing, measuring the height, measuring the ultrasonic transit time, multiplying, and destroying for at least two specimens, to establish a set of regression data; and performing a single variable regression between a function of the carrier variable and the measured fraction of phases present in the specimen, for the set of regression data.

In a related approach, a multivariate calibration relationship incorporating both consolidated height and consolidated transit time is formed, and used in the evaluation of working specimens. In accordance with this aspect of the invention, a method for establishing a primary calibration relationship useful in finding the fraction of phases present in a composite material comprises the steps of pressing a specimen of a composite material between two probes with a pressure sufficient to remove voids that may be present in the composite material prior to the application of the pressure, and, while so pressing, measuring the height of the specimen between the probes, and measuring the ultrasonic transit time through the thickness of the specimen in the region between the probes; destroying the specimen and measuring the fraction of phases present in the specimen; repeating the steps of pressing, measuring the height, measuring the ultrasonic transit time, and destroying for at least two specimens, to form a regression data set; and performing a multivariate regression of the regression data set using the measured fraction of a phase as the dependent variable and the height and transit time as the two independent variables.

The calculation of the multivariate regression calibration relation is complicated by the fact that the design matrix of the specimen measurements is nearly singular, leading to unstable parameter estimates. The ridge regression technique, known in the field of statistics but previously not applied to the determination of composite phase fractions, provides the preferred mathematical basis for conducting these analyses.

In all of these analytical techniques, the height and ultrasonic transit time information can be normalized by a factor such as number of plies to account for differing structures of the test specimens.

One important class of composite materials is single layers of prepreg sheets formed of fibers all oriented in the same direction (i.e., unidirectional fibers) and lying in the plane of the sheet, in a partially cured organic material matrix. These single layers are typically only about 0.005 inches thick, and are therefore very difficult to measure accurately by conventional thickness measurement and ultrasonic transit time apparatus. It has been found that measurements performed on a multilayered stack of the single-ply prepreg sheets can produce a high degree of accuracy when the measurements are used for the calibration relationships described earlier and also for others. However, the sheets must be stacked such that the fibers in adjacent layers are crossways to each other. That is, in any two adjacent layers of the stack, the fibers cannot be parallel, and are preferably at 90 degrees to each other.

In accordance with this aspect of the invention, a method for establishing a primary calibration relationship useful in finding the fraction of phases present in a composite material comprises the steps of furnishing a piece of single-ply prepreg composite material having uniaxial fibers therein; forming a multilayer test specimen from the single-ply piece by arranging the single plies one upon the other, such that the uniaxial fibers are not parallel to each other in any two adjacent layers; nondestructively measuring a property of the test specimen that varies with the fraction of fibers and the number of layers of the test specimen; destructively measuring the fraction of the phases present in the specimen; repeating the steps of furnishing, forming, nondestructively measuring, and destructively measuring on a total of at least two specimens to form a data set; and correlating the nondestructively measured property with the fraction of the phases determined in the step of destructively measuring for the values of the data set to establish the primary calibration relation. The stack of pieces is typically formed by folding or cutting and stacking.

The approaches discussed herein are utilized to provide calibration data that is in turn used to make very accurate nondestructive measurements of the fractions of the phases of working specimens of composite materials. Other features and advantages of the invention will be apparent from the following more detailed description of the preferred embodiment, taken in conjunction with the accompanying drawings, which illustrate, by way of example, the features of the invention.

DETAILED DESCRIPTION OF THE PREFERRED EMBODIMENTS

In the methods of the invention for establishing a primary calibration relation, the height (or equivalently stated, the thickness) of the specimen and the time for an ultrasonic wave to pass therethrough (the "ultrasonic transit time", also sometimes termed the "time of flight" of an ultrasonic wave) must be measured. These measurements are preferably made under the consolidation conditions set forth in U.S. Pat. No. 4,856,335. Briefly, the specimen is placed between two ultrasonic transducers that act as probes, one of which is stationary and the other movable. A compressive force is applied to the specimen through the movable transducer at a fixed application rate, forcing the transducers together. Height measurements are continuously made by monitoring the movement of the movable transducer. At the same time, the ultrasonic transit time for an ultrasonic wave to travel from one transducer to the other through the specimen is continuously measured. (Equivalently, only a single transducer can be used to obtain ultrasonic reflection measurements, with the specimen supported on a fixed support. Both the transducer and the support are considered "probes" in this case.)

The height and transit time measurements for the "optimal consolidation" thickness are selected for use in forming calibration relationships. The "optimal consolidation" thickness is reached when voids in the specimen are removed by compression. Preferably, the respective measurements are taken before partially cured matrix material begins to extrude from the specimen at times well past the attaining of the optimum consolidation thickness.

If the calibration is formed from data taken substantially before the optimal consolidation thickness is reached, the calibration usually exhibits a wide degree of scatter of the data points. For a prepreg specimen, about 5-10 percent of reduction in original height during compression is typically required before the optimal consolidation point is reached. For a previously cured specimen, very little compression is required before the optimal consolidation point is reached. The '335 patent provides a mathematical procedure for determining when the optimal consolidation point is reached. The measurements can be taken at or slightly after the optimum consolidation thickness is reached. At this thickness, the specimen thickness is not rapidly decreasing, and a delay in taking the measurement past the optimum consolidation thickness is normally not unacceptable.

Figure 9:
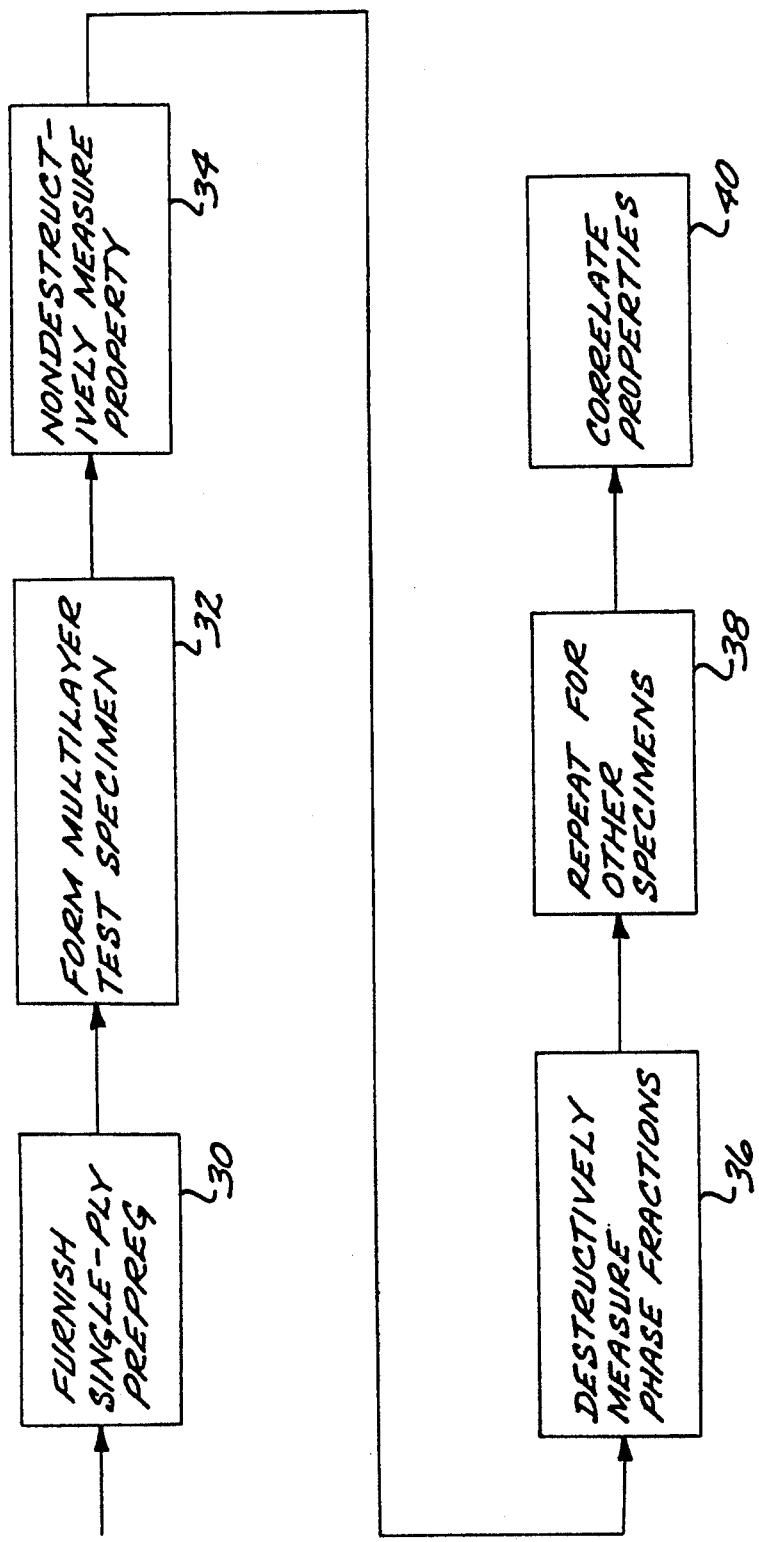
FIG. 9 is a process block diagram of a first embodiment of the invention.

To improve the accuracy of the measurements used in the calibration relations, several layers or plies of the composite material may be stacked one upon the other to increase the total material height. An increased height of material improves the accuracy of height measurements and ultrasonic transit time measurements. As shown in FIG. 9, a single ply prepreg is furnished, numeral 30, and formed into a multilayer test specimen, numeral 32. Some property of the specimen is measured nondestructively, numeral 34. The specimen is destroyed and the phase fractions measured, numeral 36. These steps are repeated for other specimens, numeral 38, and nondestructively measured properties and the respective phase fractions are correlated by one of the techniques discussed herein, numeral 40.

Where the specimen is prepreg material formed of unidirectionally oriented fibers in a flowable matrix, care must be taken to ensure that the several layers of the single-ply material are stacked properly. Specifically, the single plies must be stacked so that the fibers are not aligned in the same direction in any adjacent layers. Preferably, the plies are stacked such that the fibers in one layer are oriented at 90 degrees to those of the adjacent two layers.

Figure 1:
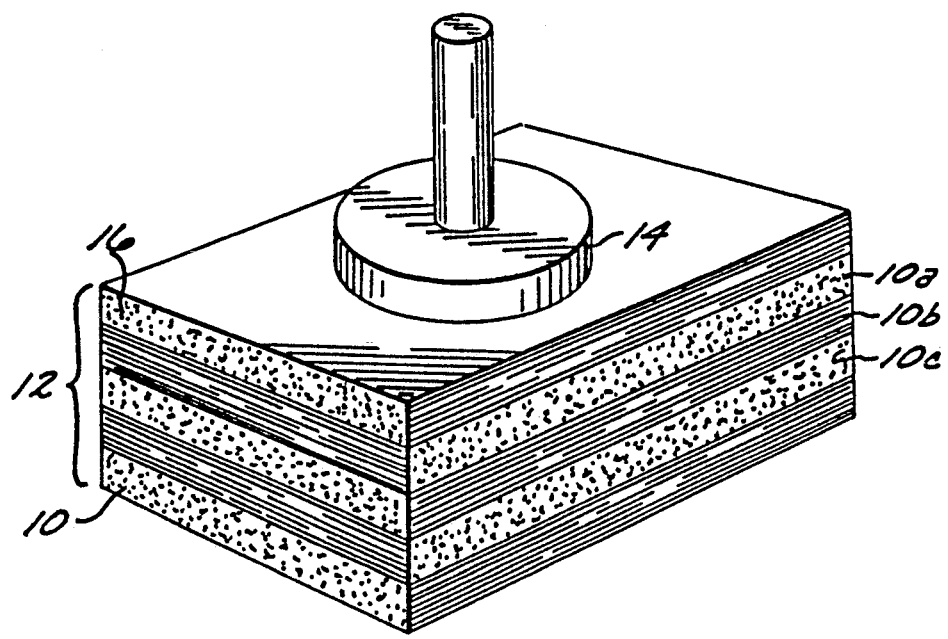
FIG. 1 is a perspective view of a composite material specimen contacted by a probe.

FIG. 1 illustrates an arrangement of five stacked single ply sheets 10 of unidirectional composite material pieces to make a specimen 12, with one of the probes or transducers 14 positioned relative to the specimen 12. The balance of the height and transit time measurement apparatus is as disclosed in U.S. Pat. No. 4,856,335. The fibers 16 in each of the pieces 10 lie within the plane of the sheet 10, and all fibers 16 within a single sheet 10 are substantially parallel to each other. However, as illustrated for the preferred embodiment, the fibers 16 within adjacent sheets, as in the pair 10a and 10b, or the pair 10b and 10c, are oriented at 90 degrees to each other. Measurements of height and ultrasonic transit time taken with the sheets 10 in such an orientation achieve better calibration relations than where the fibers in adjacent sheets are parallel to each other.

Figure 2:
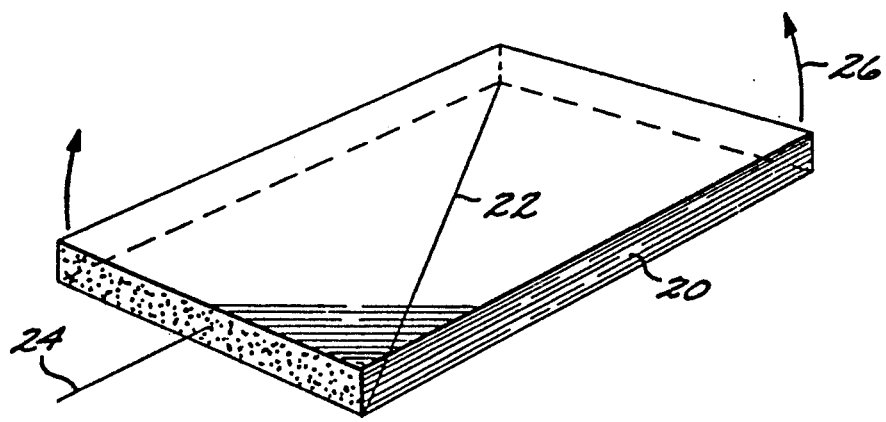
FIG. 2 is a perspective view of a prepreg composite material specimen having unidirectional fibers, indicating the folding procedure.

The preferred approach to forming a multilayered specimen is folding. FIG. 2 illustrates the preferred procedure. To form a two-layered specimen from a single sheet 20, a diagonal scribe mark 22 is first made on the sheet at 45 degrees to the fiber axis 24. The sheet is then folded about the scribe mark 22, away from the scribe mark as illustrated by the folding arrows 26. The process can be repeated as necessary to build up larger numbers of layers. Equivalently, two or more sheets 20 can be first stacked, with their fibers not in parallel relationship, and then scribed and folded as necessary. In either case, after the folding is complete, the face area of the specimen must be large enough to accommodate the area of the transducer or probe.

Figure 3:
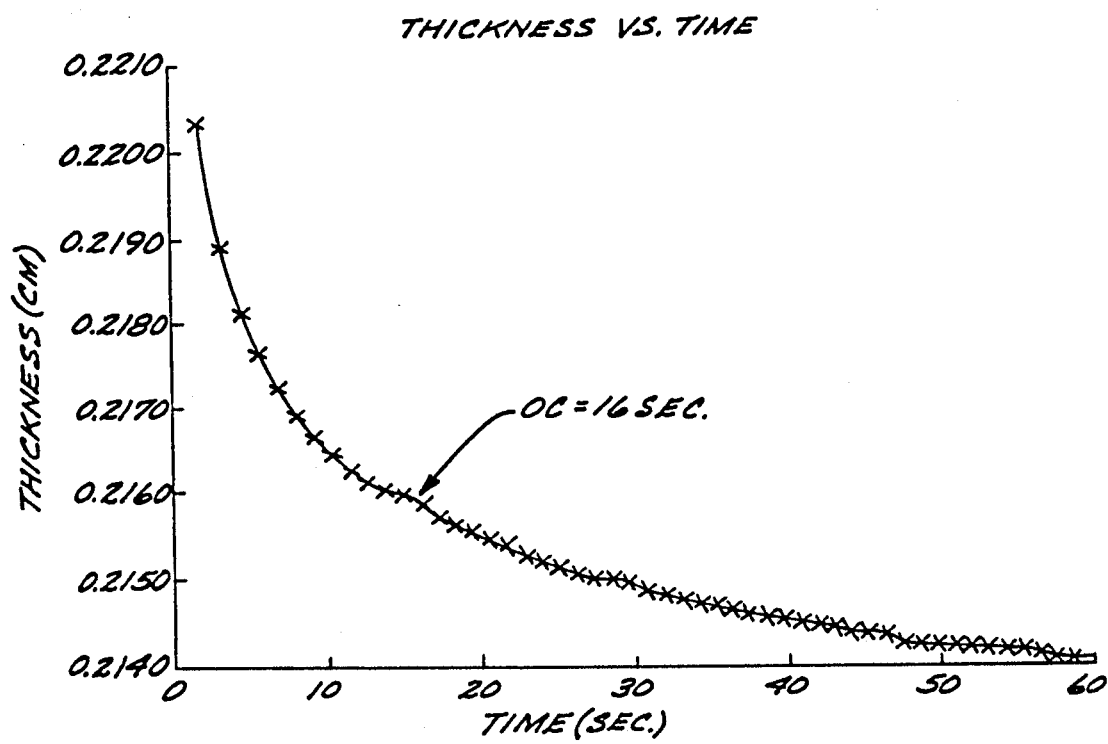
FIG. 3 is a graph of height of a specimen as a function of time after a compressive load is applied.
Figure 4:
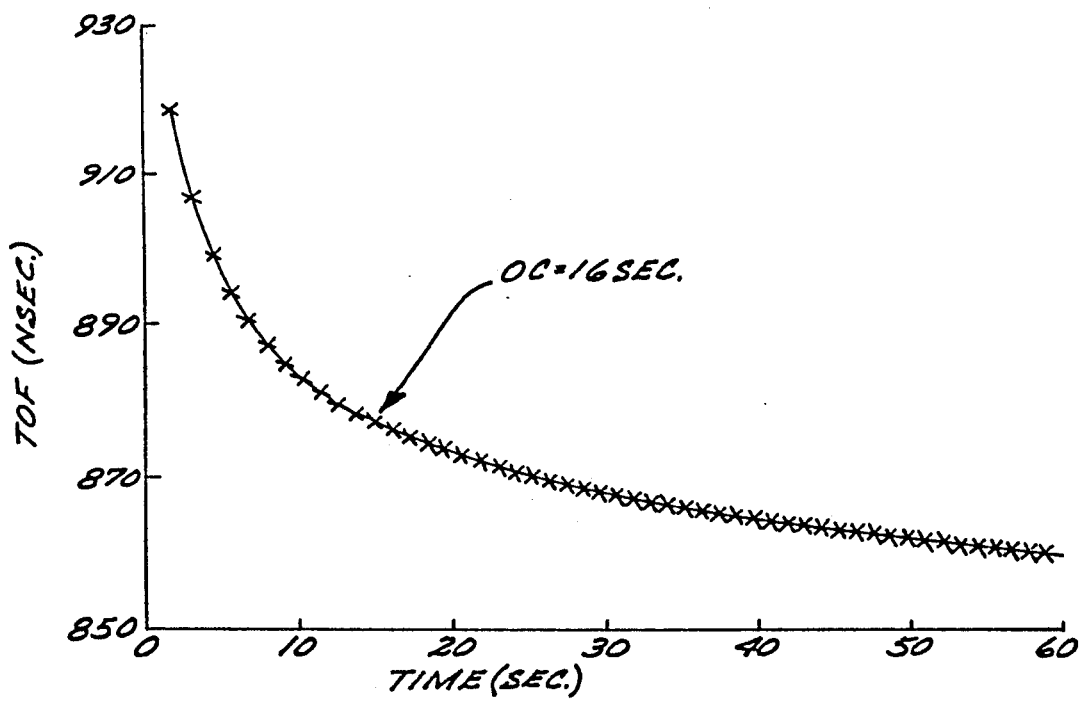
FIG. 4 is a graph of ultrasonic transit time of a specimen as a function of time after a compressive load is applied.

The apparatus of the '335 patent produces a series of measurements that can be graphed as illustrated in FIGS. 3 and 4, for height and ultrasonic transit time as a function of time after commencement of the test. An "OC" in each graph marks the point of optimal consolidation, as determined by the procedures of the '335 patent. Measurements taken at about the optimal consolidation height or thickness OC, or slightly thereafter, achieve the best calibration relationships.

If calibration specimens with different numbers of plies are to be combined in a single calibration relationship, a "normalized" value of thickness at optimal consolidation or ultrasonic transit time at optimal consolidation is computed by dividing the measured value by the number of plies stacked to form the specimen. For the example of FIG. 1, the number of plies is five. This normalization adjusts the values for variations due simply to the number of plies used.

The preferred embodiment of U.S. Pat. No. 4,794,545 achieves a calibration with a computed slowness value, the ultrasonic transit time divided by the thickness. It has also been known to perform the non-ultrasonic ratioing procedure discussed earlier, using thickness measurements. Neither approach disclosed heights or ultrasonic transit times achieved at optimal consolidation.

The calibration relationship is formed by conducting measurements on a specimen as just described, and then destroying the specimen to determine the fraction of fibers therein using the conventional destructive measurement technique previously described, as described in the '545 and '335 patents. The data pairs height at optimal consolidation-destructively measured fiber fraction, and ultrasonic transit time at optimal consolidation-destructively measured fiber fraction each form a data point for that specimen. At least two, and preferably many, such specimens having a range of fiber fractions are measured by this technique.

According to the present invention, there are provided several improved approaches to the utilization of calibration data for such composite materials, each using all of the data gathered. The first group of approaches utilizes single-variable calibration relationships to lead to a primary calibration relation that is ultimately used with working specimens. The second approach forms a multiple variable regression primary calibration relationship which, because of the nature of the variables, typically requires the application of specialized computational techniques.

Single variable regression

In a first approach, a first regression relation is formed with the data set for the calibration specimens that includes data pairs of measured height and measured phase fraction. A second regression relation is formed with the data set that includes data pairs of measured ultrasonic transit time and measured phase fraction. In each case, conventional single-variable regression techniques with a polynomial regression of the form $$PRV = D_o + D_1(\text{var}) + D_2(\text{var})^2$$

are preferred, where PRV is the measured percentage of resin by volume, $D_o$, $D_i$, and $D_2$ are adjustable constants determined in the regression analysis, and "var" is the variable that may be nondestructively measured, such as height or ultrasonic transit time.

Figure 5:
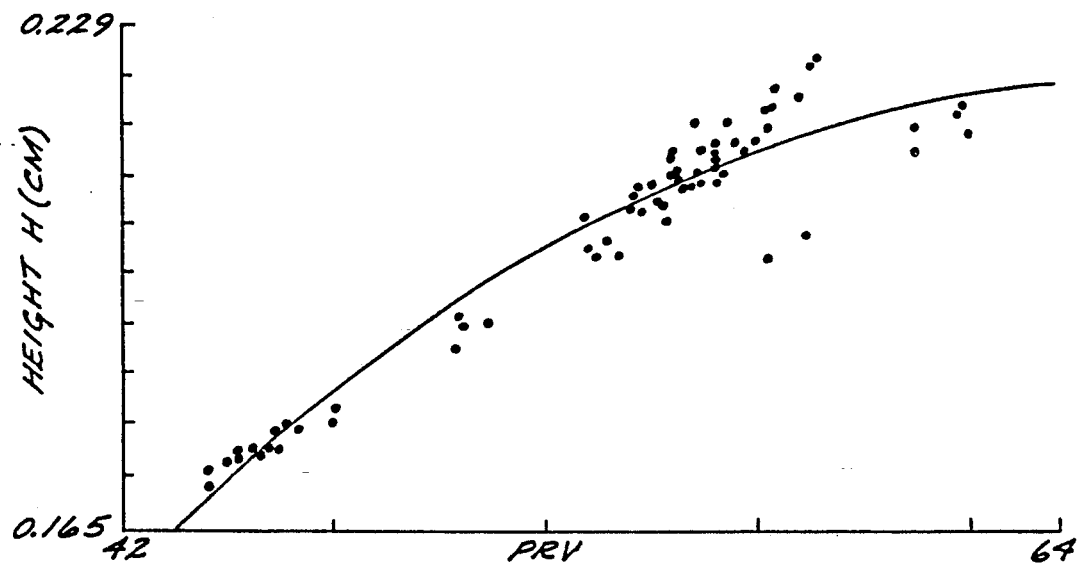
FIG. 5 is a calibration relation based upon nondestructive measurement of height at optimum consolidation.
Figure 6:
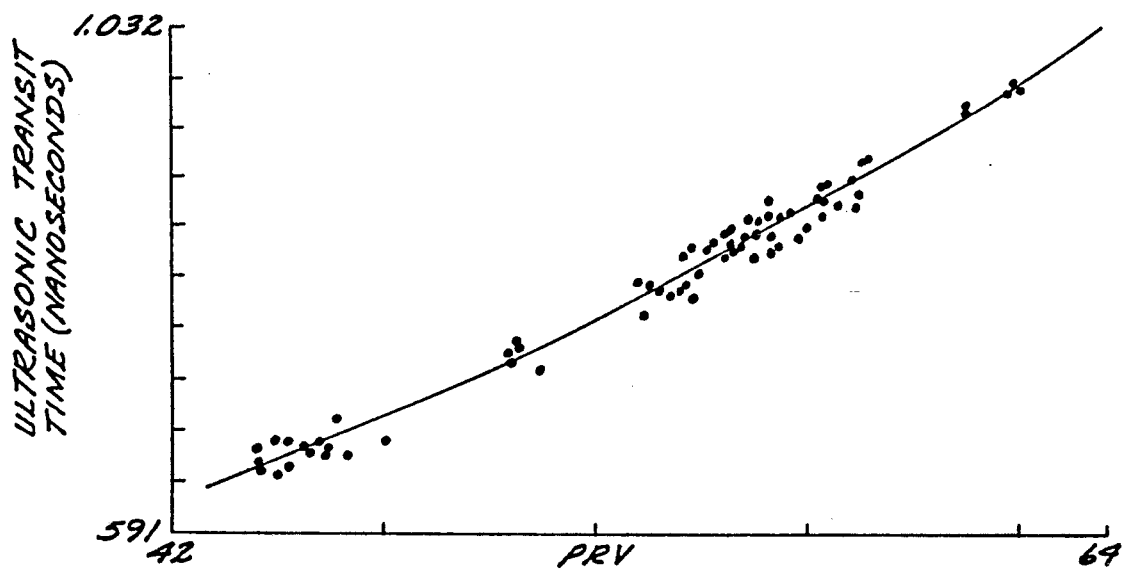
FIG. 6 is a calibration relation based upon nondestructive measurement of ultrasonic transit time at optimum consolidation.

One form of a single variable calibration relationship for a data series is illustrated in FIG. 5 for the consolidated height, and in FIG. 6 for the consolidated ultrasonic transit time. FIGS. 5 and 6 employ actual data from specimens having glass fibers in an epoxy matrix. In each case, a calibration line of the above form was determined from the data points. Later, when working specimens are to be evaluated, only the height at optimal consolidation or the ultrasonic transit time at optimal consolidation need be measured in a nondestructive manner, and the fraction of fibers in the specimen is obtained from the calibration relationship.

It has been observed during the development of a body of calibration data on different fiber/matrix combinations that in some cases the calibration relationship formed using ultrasonic transit time data is superior to that formed using height data, and in other cases the other approach is superior. In the results depicted in FIGS. 5 and 6, the calibration relationship formed with ultrasonic transit time data has a smaller mean square error than the calibration relationship formed with height measurement data. Even with statistical removal of outlying points, the calibration relationship formed with ultrasonic transit time data remains superior. When working specimens are measured, for the case depicted in FIGS. 5 and 6, fiber fractions can be determined within the required specifications for the data set of FIG. 5, but not that of FIG. 6. In other cases, the reverse is true, and the calibration formed with height data is superior.

Figure 7:
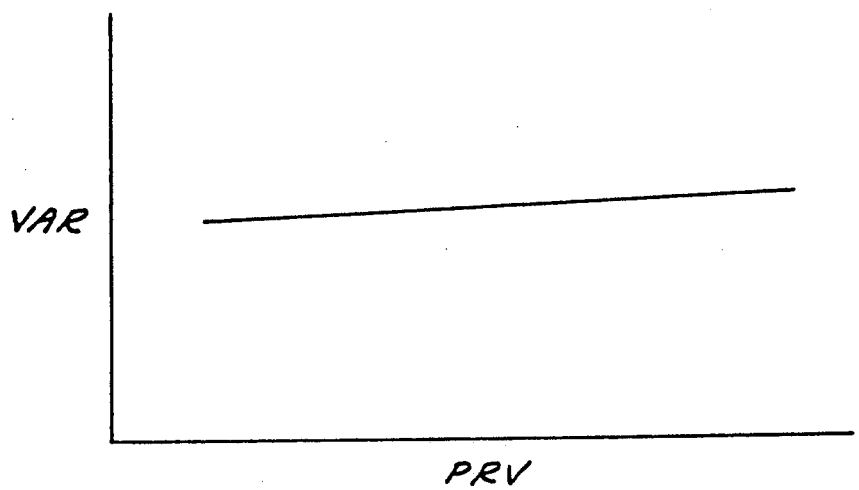
FIG. 7 is a schematic graph showing an inoperable calibration relationship having an insufficient slope.
Figure 8:
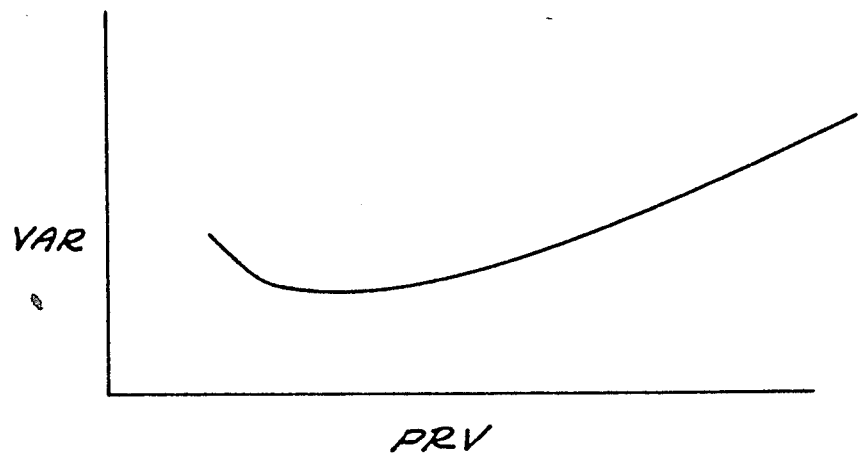
FIG. 8 is a schematic graph showing an inoperable calibration relationship having multiple

In some instances, other types of problems may exist in one of the calibration relationships but not in the other, rendering the one useless. FIG. 7 is a schematic calibration relationship wherein the average first derivative at any point of interest is so small that it cannot be used to obtain accurate values of the fiber fraction. FIG. 8 is a schematic calibration relationship wherein the first derivative of the calibration line changes sign, so that there are multiple roots when the relationship is used for evaluating working specimens. The situations of both FIGS. 7 and 8 have been observed in some composite materials systems and calibrations.

The cause for this range of behaviors in various composite materials systems is not known with certainty. Which of these calibration relationships, or others that might be formed, is superior cannot be predicted with certainty at the present time.

Another type of problem that arises is an apparatus error or failure. For example, even though the transducer used to measure height drifts such that its measurements are not accurate, the ultrasonic transit time is not affected. In this case, the height calibration relation would be unreliable, while the transit time relation would be fully operable.

Figure 10:
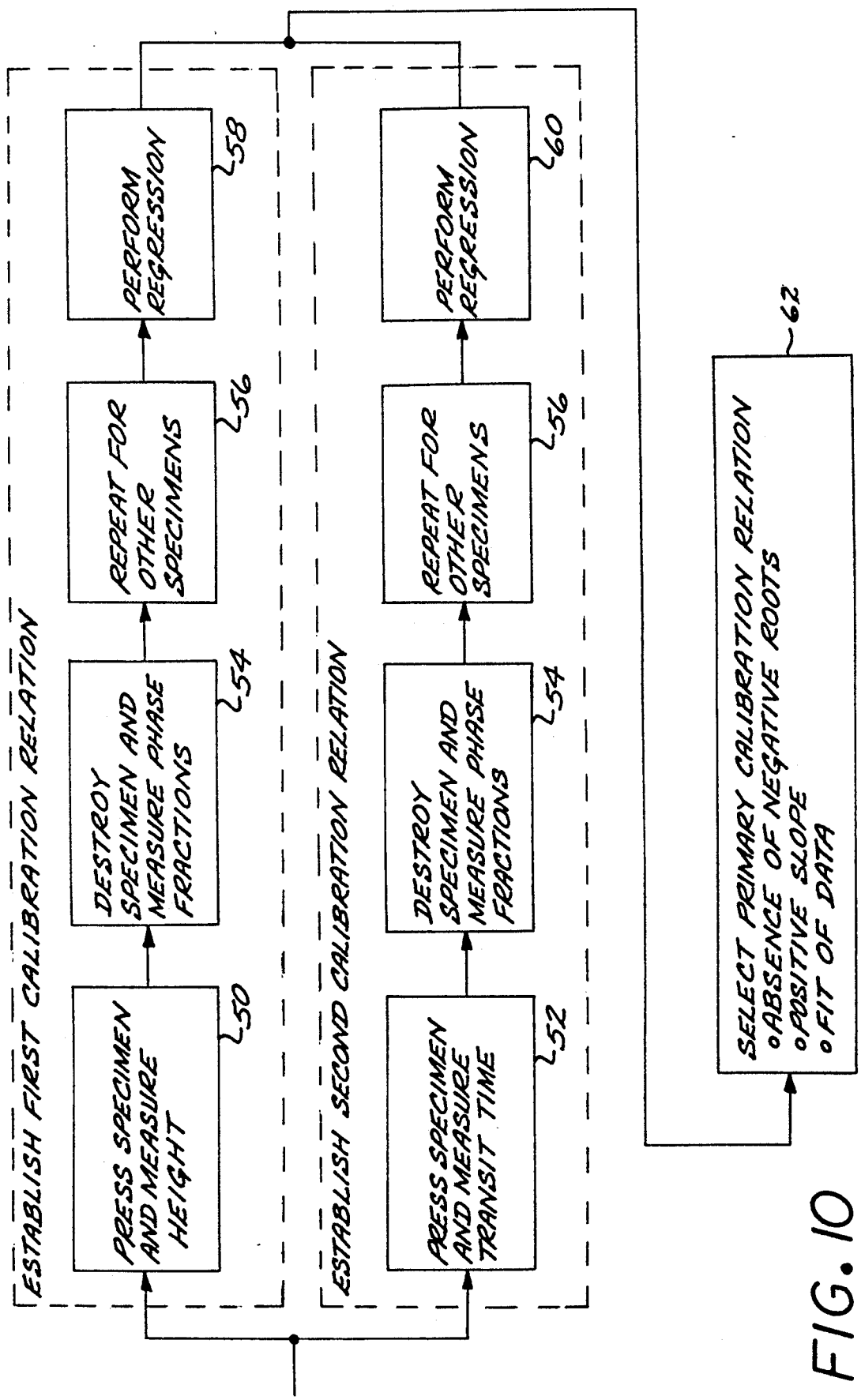
FIG. 10 is a process block diagram of another embodiment of the invention.

According to one aspect of the present invention, illustrated in FIG. 10, the two calibration relationships are formed, and the better used in actual evaluations of working specimens. One of the calibration relationships is between normalized height at optimal consolidation and phase fraction, and the other is between normalized ultrasonic transit time at optimal consolidation and phase fraction. Each specimen is pressed and, simultaneously, its height is measured, numeral 50, and transit time is measured, numeral 52. The specimen is destroyed and its phase fraction measured, numeral 54. These steps are repeated for other specimens, numeral 56, and regressions between height and phase fraction, numeral 58, and transit time and phase fraction, numeral 60, are performed. Since both measurements are made using the apparatus of the referenced patents and the data is handled by a computer, the labor to prepare these two calibrations is no greater than to prepare only one of them.

The better of the two calibration relationships is selected by examination of the data, or with computer routines designed to implement the selection procedures used by a human being, numeral 62. Each calibration relationship is first evaluated to be certain that it does not present multiple roots, as depicted in FIG. 8, for the range of interest. Then each is evaluated to be certain that it has a sufficient slope, as discussed in relation to FIG. 7. Finally, the goodness of fit is evaluated with the correlation coefficient of the data to the calibration line, or some other statistical test, to choose between calibration relationships such as shown in FIGS. 5 and 6, which meet both of the prior tests.

To date, over 60 composite materials systems have been evaluated according to this procedure. In every case, at least one of the calibration relationships discussed herein is operable to yield the desired +/−0.5 percentage point accuracy in evaluation of working specimens. In many cases one of the relationships is not operable to yield that result and cannot be used, but the other is sufficient. No basis for predicting which relationship is better has been identified.

Figure 11:
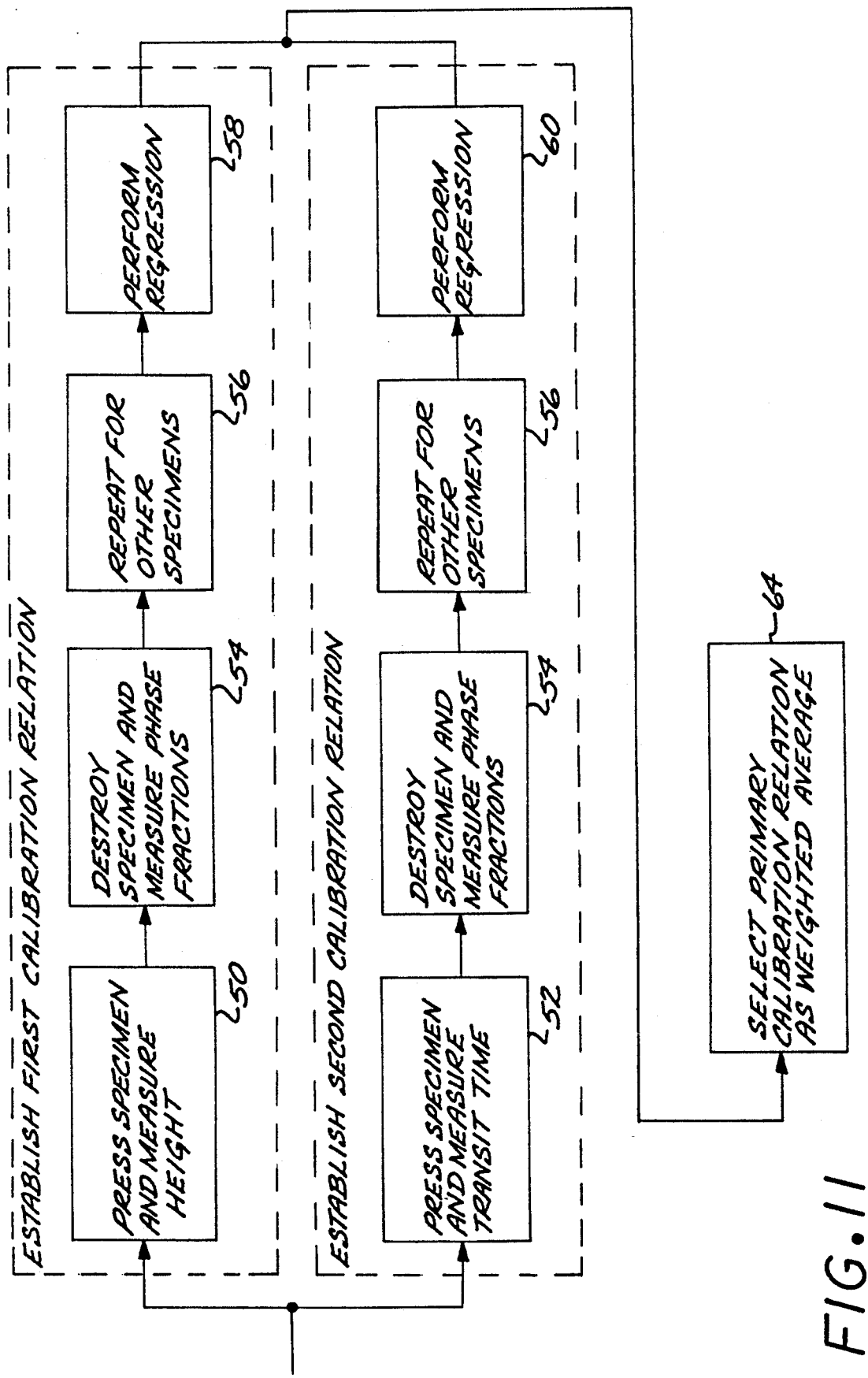
FIG. 11 is a process block diagram of another embodiment of the invention.

The measured height and ultrasonic transit time can be utilized in single-variable regression relations in other ways. In one, approach illustrated in FIG. 11, the two calibration relations discussed previously, the height-phase fraction and ultrasonic transit time-phase fraction, are prepared, using the steps 50, 52, 54, 56, 58, and 60 discussed previously. The primary calibration relation includes both of the single-variable regression relations. This approach is used only when neither of these calibration relations has multiple roots or an unacceptably low slope. The primary calibration relation is then used by finding the phase fraction for each working specimen from each calibration relation, as described in U.S. Pat. No. 4,794,545, yielding two different values of the phase fraction. The final phase fraction is determined as a weighted average of the two values, numeral 64. The weighting factor for each is preferably 0.5, but can be adjusted to place a higher weighting on the value determined from the relation with the higher correlation coefficient.

Figure 12:
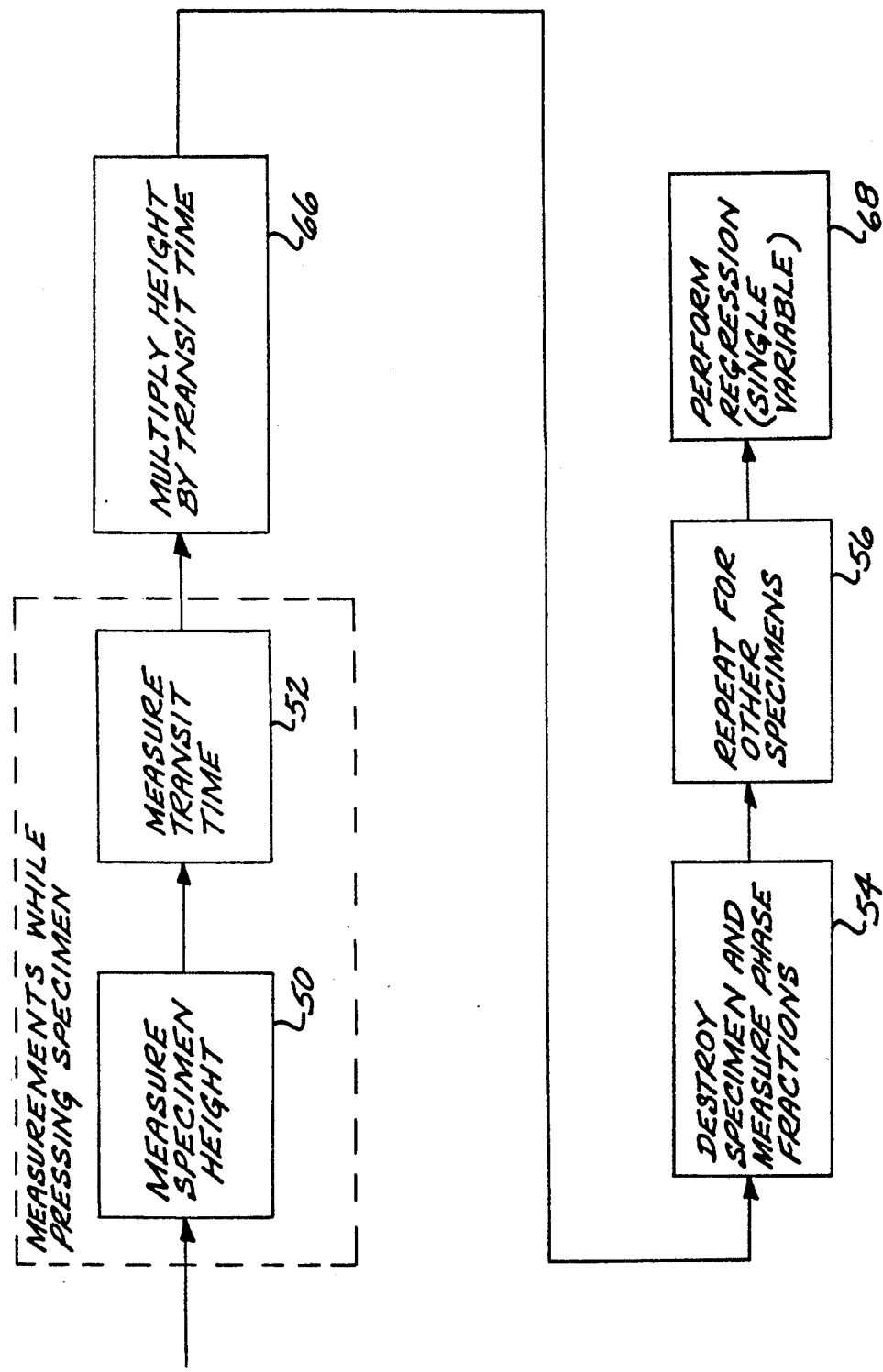
FIG. 12 is a process block diagram of another embodiment of the invention.

In another approach illustrated in FIG. 12, the consolidated height and ultrasonic transit time measurements are multiplied together to form a carrier variable. The specimen height is measured, numeral 50, and the transit time is measured, numeral 52, while pressing the specimen. The height and transit time are multiplied together, numeral 66. The specimen is destroyed and the phase fractions measured, numeral 54. This process is repeated for other specimens, numeral 56. A conventional single-variable regression of the type discussed previously is performed, numeral 68, for the data set of some function of the carrier variable, preferably its square root, as "var", and the measured phase fraction such as PRV. Other functions of the carrier variable can be used, but the square root of the product yields a quantity having the same dimensionality as the original variables.

Single-variable height and ultrasonic transit time calibrations were prepared for two series of kevlar fiber/epoxy matrix specimens. A single-variable calibration for the product of height and ultrasonic transit time was also calculated. All three calibrations were relative to the destructively measured percent resin by volume (PRV). The results are summarized in the table:

| Calibration | Correlation coefficient | |
|---|---|---|
| | Series 1 | Series 2 |
| Height/PRV | .9932 | .98777 |
| Transit Time/PRV | .99195 | .99043 |
| Product/PRV | .99295 | .99158 |

For Series 1 specimens, all three approaches produced an acceptable correlation coefficient. For Series 2 specimens, the calibration based upon height had a correlation coefficient of less than 0.99, and the calibration based upon the product of measurements was superior to the other approaches.

The nearer the correlation coefficient is to 1.0, the more accurate will be the PRV values determined for working specimens. In these two series of specimens, any of these calibration techniques would be operable to yield acceptable PRV values, but in other cases the product calibration technique is preferred.

Multiple variable regression

Statistical development of multiple-variable regressions typically requires the formation of a matrix with all of the measurements, and inversion of that matrix or similar manipulation of the data. Thus, in a standard multiple regression, parameter estimates bj are represented in matrix form as $$bj = (X^T X)^{-1} X^T Y$$

where X is a matrix of the TOF (time of flight or ultrasonic transit time) and H (height) values, Y is the dependent variable PRV, and T denotes a transpose matrix.

In the present case, because the normalized height at optimal consolidation and the normalized ultrasonic transit time at optimal consolidation are closely correlated in the sense of being nearly linearly dependent, the matrices formed from them are nearly singular. The inversion of near-singular matrices can lead to erroneous results unless special precautions are taken.

The preferred approach to the multiple regression analysis of height and ultrasonic transit time data is based upon the "ridge regression" technique described in detail in A. E. Hoerl and R. W. Kennard, "Ridge Regression: Biased Estimation for Nonorthogonal Problems", *Technometrics*, vol. 12, pages 55–82 (1970) and also in N. R. Draper and H. Smith, "Applied Regression Analysis", John Wiley & Sons, pages 313–324 (copyright 1966, 1981), whose discussions are incorporated by reference.

In the present approach, the preferred technique is a nonlinear ridge regression of an equation of the form $$PRV = B_0 + B_1 x_1 + B_2 x_2 + B_3 (x_1)^2 + B_4 (x_2)^2.$$

where $B_0$, $B_1$, $B_2$, and $B_3$ are adjustable constants and $x_1$ and $x_2$ are the carrier variables height and ultrasonic transit time.

Ridge regression introduces biased estimators to avoid problems of design matrices that are close to singular. The multiple variable ridge regression of a set of data is expressed in matrix form as $$b_z(c) = (Z^T Z + cI)^{-1} Z^T Y$$

where $b_z$ are the estimators, c the "ridge estimator", I the identity matrix, and Z a centered and scaled "design matrix". The Z matrix is defined as $$Z = \begin{bmatrix} z_{11} & z_{12} & z_{13} & z_{14} \\ . & . & . & . \\ . & . & . & . \\ . & . & . & . \\ z_{n1} & z_{n2} & z_{n3} & z_{n4} \end{bmatrix}$$

with the matrix components defined as $$z_{i1} = (x_{i1} - x_{i1})/s_{x1}(n-1)^{\frac{1}{2}}$$
$$z_{i2} = (x_{i2} - x_{i2})/s_{x2}(n-1)^{\frac{1}{2}}$$
$$z_{i3} = (z_{i1})^2$$
$$z_{i4} = (z_{i2})^2$$
$$Y = y - y/s_y(n-1)^{\frac{1}{2}}$$

where $s_{x1}$, $s_{x2}$, and $s_y$ are the sample standard deviation of the $x_1$, $x_2$, and y, repeatedly. Here $x_1$ corresponds to TOF or consolidated time of flight, $x_2$ corresponds to H or consolidated height, and Y corresponds to PRV or some directly related indicator of phase fraction, such as percentage of resin by weight, percentage of fiber by volume, or percentage of fiber by weight.

The best value of c is selected as $$c^* = ks^2/(b_*(0)^T b_*(0)).$$

The value of k is 4 in this case. $s^2$ is the residual mean square obtained from the standard least squares, or $$s^2 = \Sigma(Y - \hat{Y})^2/n - 2$$

where Y is the observed results and $\hat{Y}$ is the estimated regression data from a conventional multiple regression. In the expression for $c^*$, $$b_*(0) = (Z^T Z)^{-1} Z^T Y$$
$$= \{b_{1*}(0), b_{2*}(0)$$
$$b_{3*}(0), b_{4*}(0)\}^T$$

The centered and scaled model $$Y = b_{1*}(c)z_1 + b_{2*}(c)z_2 + b_{3*}(c)z_3 + b_{4*}(c)z_4$$

is converted to the calibration model $$PRV = b_0 + b_1 x_1 + b_2 x_2 + b_3(x_1)^2 + b_4(x_2)^2$$

through the conversion $$b_j(c) = b_{j*}(c)/(S_{ij})^{\frac{1}{2}}$$

with j = 1, 2, 3, 4. Here $S_{ij}$ is calculated as $$S_{ij} = \sum_{i=1}^{n} (Z_{ji} - \bar{Z}_j)^2$$

and $b_0(c)$ is calculated as $$b_0(c) = \bar{Y} - \sum_{j=1}^{4} b_j(c)\bar{Z}_j.$$

Figure 13:
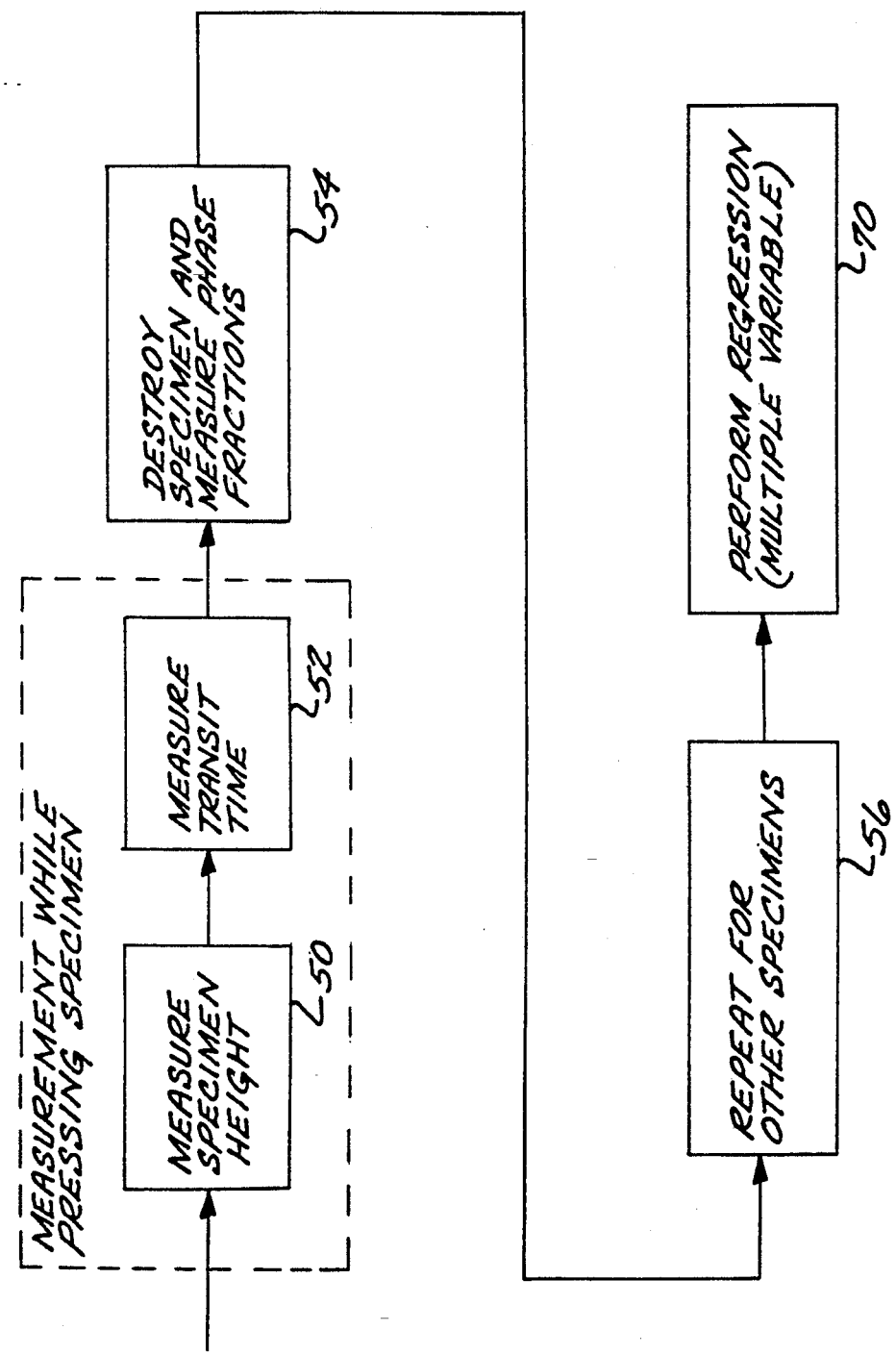
FIG. 13 is a process block diagram of another embodiment of the invention.

To evaluate the operability of the nonlinear ridge regression analysis, height and ultrasonic time of flight measurements were made of a group of 26 kevlar fiber-/epoxy resin matrix composite specimens using the optimal consolidation technique as discussed above. The results were selected for use in evaluating the ridge regression because both the height and ultrasonic calibration relations were operable for this particular materials system. As shown in FIG. 13, the specimen height and transit time are measured, numerals 50 and 52. The specimen is destroyed and the phase fractions measured, numeral 54. These steps are repeated for other specimens, numeral 56. A multiple regression is then performed, numeral 70. Calibration relations were determined by single-variable regressions as $$PRV(H) = -21.82719 + 468.61566 H - 533.16934 H^2$$

$$PRV(TOF) = -8.79816 + 87.3753 TOF - 22.62148 TOF^2.$$

A calibration relation was determined by the ridge regression as $$PRV(H,TOF) = 14.730 + 66.801 H + 11.853 TOF + 166.511 H^2 + 6.716 TOF^2.$$

The PRV for each of the original 26 data points was calculated for each of these calibrations, using each measurement as though it were a working specimen. The mean difference between PRV(H) and PRV(TOF) was 0.17 percentage points, the mean difference between PRV(H) and PRV(H,TOF) was 0.15 percentage points, and the mean difference between PRV(TOF) and PRV(H,TOF) was 0.15 percentage points, indicating excellent agreement.

The ridge regression approach provides a methodology for forming the primary calibration that directly utilizes all of the measured data, and yields results close to those of the single-variable regression, for this case where the results of each single-variable technique are in good agreement.

Various approaches to calculating the ridge estimator are possible, and may be applicable to multiple variable regression of composite material data. The approach set forth herein is the best mode known to the inventors at the present time.

The analysis techniques discussed herein are particularly useful for composite materials in the prepreg state. The approach described in U.S. Pat. No. 4,794,545 using a calibration parameter such as ultrasonic slowness remains preferred for the majority of situations of cured composite materials, where the number of plies often cannot be readily determined.

The present invention thus provides a reliable approach to the determination of calibration relationships for the determination of phase fraction in composite materials systems, and particularly for prepreg materials where such determination has previously been difficult. In one approach, all of the different techniques described herein are calculated from the data measurements to determine the optimal primary calibration relation for each particular system, and then that selected relation is used for the evaluation of working specimens. Instrument drift and error can also be determined by examining the various primary calibrations resulting from the different techniques. Although particular embodiments of the invention have been described in detail for purposes of illustration, various modifications may be made without departing from the spirit and scope of the invention. Accordingly, the invention is not to be limited except as by the appended claims.

What is claimed is:

1. A method for establishing a primary calibration relationship useful in finding the fraction of phases present in a composite material, comprising the steps of:
   establishing a first calibration relation between a consolidated height of a specimen of a composite material and the fraction of phases in the specimen by the substeps of
   pressing the specimen between two probes with a pressure sufficient to remove voids that may be present in the composite material prior to the application of the pressure and measuring the height of the specimen between the probes,
   destroying the specimen and measuring the fraction of phases present in the specimen,
   repeating the steps of pressing and measuring the height, and destroying for at least two specimens, to form a first regression data set, and
   performing a single variable regression between the measured height of the specimen and the measured fraction of phases present in the specimen for the first regression data set, to form a first calibration relation;

establishing a second calibration relation between a consolidated ultrasonic transit time of a specimen of a composite material and the fraction of phases in the specimen by the substeps of pressing the specimen between two probes with a pressure sufficient to remove voids that may be present in the composite material prior to the application of the pressure and measuring the ultrasonic transit time through the thickness of the specimen between the probes, destroying the specimen and measuring the fraction of phases present in the specimen, repeating the steps of pressing and measuring the ultrasonic transit time, and destroying for at least two specimens, to form a second regression data set, and performing a single variable regression between the measured ultrasonic transit time of the specimen and the measured fraction of phases present in the specimen for the second regression data set, to form a second calibration relation; and selecting as the primary calibration relation either the first or the second calibration relation, by first determining if either the first or the second calibration relation has multiple roots or a nonpositive slope and, if so, selecting the other calibration relation, and, if neither the first or the second calibration relation has multiple roots or a nonpositive slope, then selecting the calibration relation which best fits its data.

2. The method of claim 1, wherein the same specimens are used to develop the first and second calibration relations, and wherein the probes used are ultrasonic transducers.

3. The method of claim 1, wherein the specimens of composite material are in the prepreg state.

4. The method of claim 3, wherein the specimens are formed of composite material having uniaxially oriented fibers.

5. The method of claim 4, wherein the prepreg specimens are prepared by folding single-ply pieces of prepreg in a crossed pattern to form multilayer specimens, wherein the fibers in any two adjacent layers are not parallel.

6. The method of claim 5, wherein the fibers in any two adjacent layers are oriented at 90 degrees to each other.

7. A method for establishing a primary calibration relationship useful in finding the fraction of phases present in a composite material, comprising the steps of:

pressing the specimen between two probes with a pressure sufficient to remove voids that may be present in the composite material prior to the application of the pressure, and, while so pressing, measuring the height of the specimen between the probes, and measuring the ultrasonic transit time through the thickness of the specimen in the region between the probes;

multiplying the measured height of the specimen times the measured ultrasonic transit time to form a carrier variable;

destroying the specimen and measuring the fraction of phases present in the specimen;

repeating the steps of pressing, measuring the height, measuring the ultrasonic transit time, multiplying, and destroying for at least two specimens, to establish a set of regression data; and performing a single variable regression between a function of the carrier variable and the measured fraction of phases present in the specimen, for the set of regression data.

8. The method of claim 7, wherein the function of the carrier variable is the square root of the carrier variable.

9. A method for establishing a primary calibration relationship useful in finding the fraction of phases present in a composite material, comprising the steps of:

establishing a first calibration relation between a consolidated height of a specimen of a composite material and the fraction of phases in the specimen by the substeps of pressing the specimen between two probes with a pressure sufficient to remove voids that may be present in the composite material prior to the application of the pressure and measuring the height of the specimen between the probes, destroying the specimen and measuring the fraction of phases present in the specimen, repeating the steps of pressing and measuring the height, and destroying for at least two specimens, to form a first regression data set, and performing a single variable regression between the measured height of the specimen and the measured fraction of phases present in the specimen for the first regression data set, to form a first calibration relation;

establishing a second calibration relation between a consolidated ultrasonic transit time of a specimen of a composite material and the fraction of phases in the specimen by the substeps of pressing the specimen between two probes with a pressure sufficient to remove voids that may be present in the composite material prior to the application of the pressure and measuring the ultrasonic transit time through the thickness of the specimen between the probes, destroying the specimen and measuring the fraction of phases present in the specimen, repeating the steps of pressing and measuring the ultrasonic transit time, and destroying for at least two specimens, to form a second regression data set, and performing a single variable regression between the measured ultrasonic transit time of the specimen and the measured fraction of phases present in the specimen for the second regression data set, to form a second calibration relation; and selecting as the primary calibration relation the combination of the first and the second calibration relations, the phase fraction for a working specimen being a weighted average of the phase fractions independently determined from the first and the second calibration relations.

10. The method of claim 9, wherein each phase fraction is equally weighted in forming the weighted average.

11. A method for establishing a primary calibration relationship useful in finding the fraction of phases present in a composite material, comprising the steps of:

pressing a specimen of a composite material between two probes with a pressure sufficient to remove voids that may be present in the composite material prior to the application of the pressure, and, while so pressing, measuring the height of the specimen between the probes, and measuring the ultrasonic transit time through the thickness of the specimen in the region between the probes;

destroying the specimen and measuring the fraction of phases present in the specimen;

repeating the steps of pressing, measuring the height, measuring the ultrasonic transit time, and destroying for at least two specimens, to form a regression data set; and performing a multivariate regression of the regression data set using the measured fraction of a phase as the dependent variable and the height and transit time as the two independent variables.

12. The method of claim 11, wherein the step of performing utilizes a ridge multivariate regression.

13. The method of claim 11, wherein the specimens of composite material are in the prepreg state.

14. The method of claim 13, wherein the specimens are formed of composite material having uniaxially oriented fibers.

15. The method of claim 14, wherein the prepreg specimens are prepared by folding single-ply pieces of prepreg in a crossed pattern to form multilayer specimens, wherein the fibers in any two adjacent layers are not parallel.

16. The method of claim 15, wherein the fibers in any two adjacent layers are oriented at 90 degrees to each other.

17. A method for establishing a primary calibration relationship useful in finding the fraction of phases present in a composite material, comprising the steps of:

furnishing a piece of single-ply prepreg composite material having uniaxial fibers therein;

forming a multilayer test specimen from the single-ply piece by arranging the single plies one upon the other, such that the uniaxial fibers are not parallel to each other in any two adjacent layers;

nondestructively measuring a property of the test specimen that varies with the fraction of fibers and the number of layers of the test specimen;

destructively measuring the fraction of the phases present in the specimen;

repeating the steps of furnishing, forming, nondestructively measuring, and destructively measuring on a total of at least two specimens to form a data set; and correlating the nondestructively measured property with the fraction of the phases determined in the step of destructively measuring for the values of the data set to establish the primary calibration relation.

18. The method of claim 17, wherein the step of forming is accomplished by folding the piece of single-ply composite material.

19. The method of claim 17, wherein the step of forming is accomplished by cutting the piece of single-ply composite material and stacking the cut pieces.

* * * * *